(12) United States Patent
Rodgers et al.

(10) Patent No.: US 8,207,234 B1
(45) Date of Patent: Jun. 26, 2012

(54) METHODS FOR TREATING DIABETIC FOOT ULCERS

(75) Inventors: Kathleen E. Rodgers, Long Beach, CA (US); Gere S. diZerega, San Luis Obispo, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/441,653

(22) Filed: Apr. 6, 2012

Related U.S. Application Data

(62) Division of application No. 13/364,061, filed on Feb. 1, 2012.

(60) Provisional application No. 61/438,780, filed on Feb. 2, 2011.

(51) Int. Cl.
| A61K 38/08 | (2006.01) |
|---|---|
| A61K 47/38 | (2006.01) |
| C07K 7/14 | (2006.01) |
| C07K 17/04 | (2006.01) |
| C07K 17/12 | (2006.01) |

(52) U.S. Cl. ........... 514/928; 424/488; 530/316; 930/40

(58) Field of Classification Search .................. None
See application file for complete search history.

(56) References Cited

U.S. PATENT DOCUMENTS

| 5,015,629 | A | 5/1991 | DiZerega et al. |
|---|---|---|---|
| 5,629,292 | A | 5/1997 | DiZerega et al. |
| 5,716,935 | A | 2/1998 | DiZerega et al. |
| 5,834,432 | A | 11/1998 | DiZerega et al. |
| 5,955,430 | A | 9/1999 | DiZerega et al. |
| 6,096,709 | A | 8/2000 | DiZerega et al. |
| 6,110,895 | A | 8/2000 | DiZerega et al. |
| 6,165,978 | A | 12/2000 | DiZerega et al. |
| 6,177,407 | B1 | 1/2001 | Rodgers et al. |
| 6,248,587 | B1 | 6/2001 | Rodgers et al. |
| 6,258,778 | B1 | 7/2001 | Rodgers et al. |
| 6,335,195 | B1 | 1/2002 | Rodgers et al. |
| 6,444,646 | B1 | 9/2002 | DiZerega et al. |
| 6,455,500 | B1 | 9/2002 | Rodgers et al. |
| 6,455,501 | B1 | 9/2002 | DiZerega et al. |
| 6,475,988 | B1 | 11/2002 | Rodgers et al. |
| 6,482,800 | B1 | 11/2002 | Rodgers et al. |
| 6,498,138 | B1 | 12/2002 | Rodgers et al. |
| 6,566,335 | B1 | 5/2003 | Rodgers et al. |
| 6,730,775 | B1 | 5/2004 | DiZerega et al. |
| 6,762,167 | B1 | 7/2004 | Rodgers et al. |
| 6,821,953 | B1 | 11/2004 | DiZerega et al. |
| 6,916,783 | B2 | 7/2005 | Rodgers et al. |
| 7,022,675 | B2 | 4/2006 | DiZerega et al. |
| 7,118,748 | B1 | 10/2006 | Rodgers et al. |
| 7,173,011 | B2 | 2/2007 | Rodgers et al. |
| 7,176,183 | B2 | 2/2007 | DiZerega et al. |
| 7,338,938 | B2 | 3/2008 | Rodgers et al. |
| 7,744,927 | B2 | 6/2010 | Rodgers et al. |
| 7,776,828 | B2 | 8/2010 | Rodgers et al. |
| 7,786,085 | B2 | 8/2010 | Rodgers et al. |
| 2009/0227507 | A1 | 9/2009 | Rodgers et al. |

FOREIGN PATENT DOCUMENTS

| WO | 98/33813 | 8/1998 |
|---|---|---|
| WO | 99/31125 | 6/1999 |
| WO | 99/40107 | 8/1999 |
| WO | 01/44270 | 6/2001 |
| WO | 2011/120032 | 3/2011 |
| WO | 2012/021578 | 2/2012 |

OTHER PUBLICATIONS

American Diabetes Association, Consensus development conference on diabetic foot wound care. Diabetes Care 1999; 22:1354-1360.
Pecoraro RE, Reiber GE, Burgess EM, Pathways to diabetic limb amputation: basis for prevention. Diabetes Care 1990; 13:513-521.
Rodgers KE, Roda N, Felix JC, Espinoza T, Maldonado S, diZerega GS. Histological evaluation of the effects of angiotensin peptides on wound repair in diabetic mice. Experimental Dermatology 2003; 12(6):784-790.
Rodgers K, Xiong S, Felix J, Roda N, Espinoza T, Maldonado S, diZerega GS. Development of angiotensin (1-7) as an agent to accelerate dermal repair. Wound Repair Regen 2001; 9:238-250.
Rodgers KE, Espinoza T, Felix J, Roda N, Maldonado S, diZerega GS. Acceleration of healing, reduction of fibrotic scar, and normalization of tissue architecture by an angiotensin analogue, Norleu3-A (1-7). Plast Reconstr Surg 2003; 111:1195-1206.
Wagner, FJ. A classification and treatment program for diabetic, neuropathic, and dysvascular foot problems. Am Acad of Orthopaedic Surgeons. Instructional Course Lecture 1979; 28:143-165.
Foster AV, Eaton C, McConville DO, Edmonds ME. Application of OpSite film: a new and effective treatment of painful diabetic neuropathy. Diabetes Med 1994; 11(8):768-772.
Sheehan P, Jones P, Caselli A, Giurini JM, Veves A. Percent change in wound area of diabetic foot ulcers over a 4-week period is a robust predictor of complete healing in a 12-week prospective trial. Diabetes Care 2003; 26:1879-1882.
Rodgers, KE, Abiko M, Girgis W, St. Amand KM, Campeau JD, diZerega GS. Acceleration of dermal tissue repair by Angiotensin II. Wound Repair Regen 1997; 5:175-183.
Rodgers, KE, DeCherney AH, St. Amand KM, Dougherty WR, Felix JC, Girgis W, diZerega GS. Histologic alterations in dermal repair after thermal injury: effects of topical angiotensin II. Burn Care and Rehabilitation 1997; 18:381-388.
Okuyama N, Roda N, Guerrero A, Dougherty W, Nguyen T, diZerega GS, Rodgers KE. Effect of angiotensin II on the viability, vascularity of random flaps in a rat model. Annals Plastic Surgery Res 1999; 68:913-918.
Rodgers KE, Ellefson DD, Espinoza T, Roda N, Maldonado S, diZerega GS. Effect of NorLeu3-A (1-7) on scar formation over time after full thickness incision injury in the rat. Wound Repair Regen 2005; 13:309-317.
Santos RA, Brosnihan KB, Chappell MC, Pesquero J, Chernicky CL, Greene LJ, and Ferrario CM. Converting enzyme activity and angiotensin metabolism in the dog brainstem. Hypertension 1988; 11(suppl I):I-53-I-57.

(Continued)

Primary Examiner — David Romeo
(74) Attorney, Agent, or Firm — McDonnell Boehnen Hulbert & Berghoff LLP

(57) ABSTRACT

The present invention provides methods and pharmaceutical formulations for treating diabetic foot ulcers.

12 Claims, 3 Drawing Sheets

OTHER PUBLICATIONS

Santos RAS, Brosnihan KB, Jacobsen DW DiCorleto P, and Ferrario CM. Production of Ang-(1-7) by human vascular endothelium. Hypertension 1992; 19(suppl II):II-56-II-61.

Santos et al. Characterization of a new angiotensin antagonist selective for angiotensin-(1-7): evidence that the actions of angiotensin-(1-7) are mediated by specific angiotensin receptors. Brain Res Bull 1994; 35:293-298.

Yamamoto K, Chappell MC Brosnihan KB, Ferrario CM. In vivo metabolism of angiotensin I by neutral endopeptidase (EC 3.4.24.11) in spontaneously hypertensive rats. Hypertension 1992; 19:692-696.

Chappell MC, Tallant EA, Brosnihan KB, Ferrario CM. Processing of angiotensin peptides by NG108-15 neuroblastoma X glioma hybrid cell line. Peptides 1990; 22:375-380.

Chappell MC, Jacobsen DW, Tallant EA. Characterization of angiotensin II receptor subtypes in pancreatic acinar AR42J cells. Peptides 1995; 16:741-747.

Chappell MC, Tallant EA, Brosnihan KB, Ferrario CM. Conversion of angiotensin I to angiotensin-(1-7) by thimet oligopeptidase (E.C. 3.4.24.15) in vascular smooth muscle cells. J Vasc Biol Med 1995; 5:129-137.

Daemen MJAP, Lombardi DM, Bosman FT, Schwartz SM.. Angiotensin II induces smooth muscle cell proliferation in the normal and injured rat arterial wall. Circ Res 1991; 68:450-56.

Dzau VE, Pratt R, Gibbons G, Schunkert H, Lorell B, Ingelfinger J. Molecular mechanism of angiotensin in the regulation of vascular and cardiac growth. J Mol Cell Cardiol 1989; 21 [Suppl III]:S7.

Naftilan AJ, Pratt RE, Dzau VJ. Induction of platelet-derived growth factor A-chain and c-myc gene expression by Angiotensin II in culture rat vascular smooth muscle cells. J Clin Invest 1989; 83:1419-24.

Kawahara Y, Sunako M, Tsuda T, Fukazaki H, Fukomoto Y, Takai Y. Angiotensin II induces expression of the c-fos gene through protein kinase C activation and calcium ion mobilization in cultured vascular smooth muscle cells. BBRC 1988; 150:52-9.

Mangiarua EI, Palmer VL, Lloyd LL, McCumbee WD. Platelet-derived growth factor mediates angiotensin II-induced DNA synthesis in vascular smooth muscle cells. Arch Physiol Biochem 1997; 105(2):151-7.

Su EJ, Lombardi DM, Wiener J, Daemen MJ, Reidy MA, and Schwartz MA. Mitogenic effect of angiotensin II on the rat carotid arteries and type II or III mesenteric microvessels but not type I mesenteric microvessels is mediated by endogenous basic fibroblast growth factor. Circ Res 1998; 82:321.

Rodgers LC. Driver VR, Armstrong DG. Assessment of the diabetic foot. In Krasner DL, Rodeheaver GT, Sibbald RG eds. Chronic Wound Care: A Clinical Source Book for Healthcare Professionals. 4th ed. Malvern PA: HMP Communications, 2007: 549-556.

Bolton L, McNees P, van Rijswijk L et al. Wound healing outcomes using standardized care. JWOCN 2004; 31:65-71.

Stouffer GA, Owens GK. Angiotensin II induced mitogenesis of spontaneously hypertensive rat derived cultured smooth muscle cells is dependent on autocrine production of transforming growth factor-B. Circ Res 1992; 70:820-28.

Koibuchi Y, Lee WS, Gibbons GH, Pratt RE. Role of transforming growth factor B-1 in the cellular growth response to Angiotensin II. Hypertension 1993; 21:1046-50.

Rodgers, et al., (2006) J. Peptide Res., 66(suppl. 1):41-47.

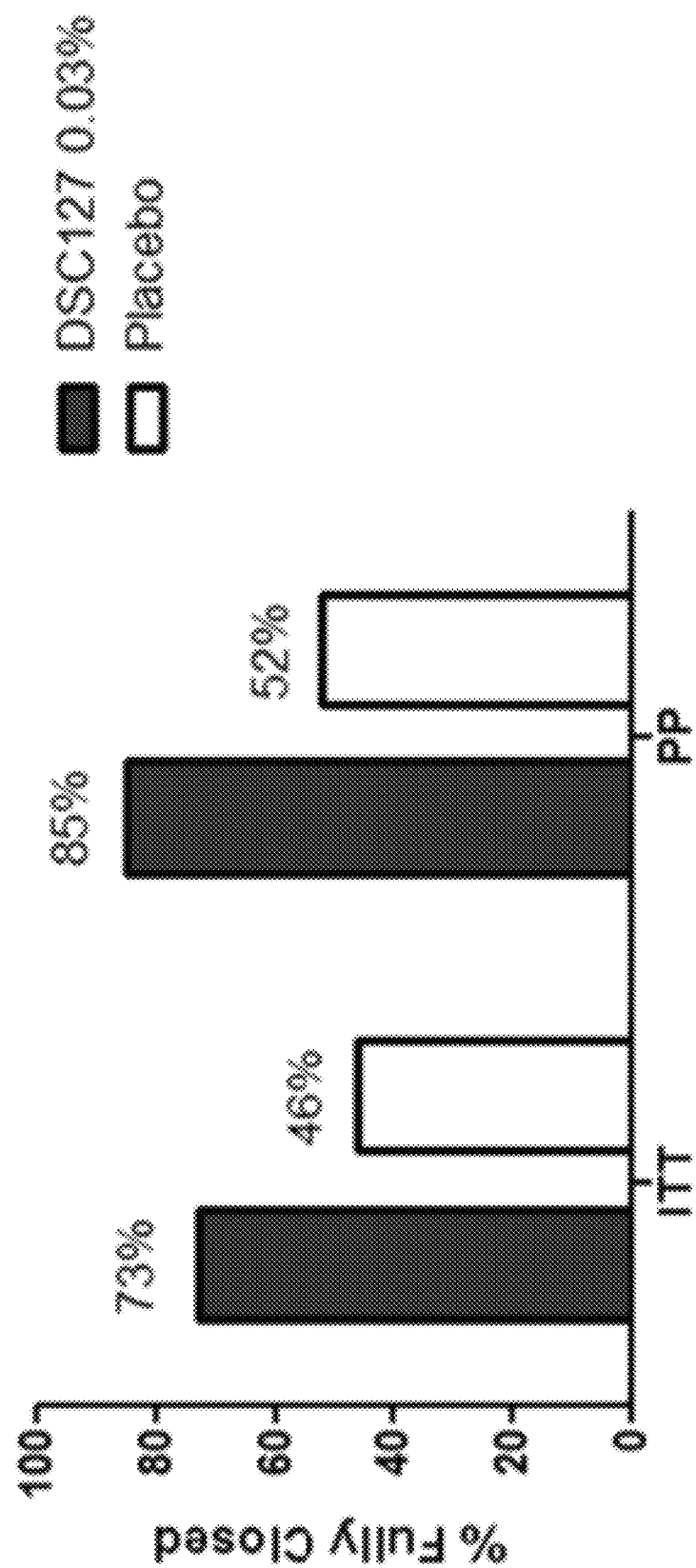

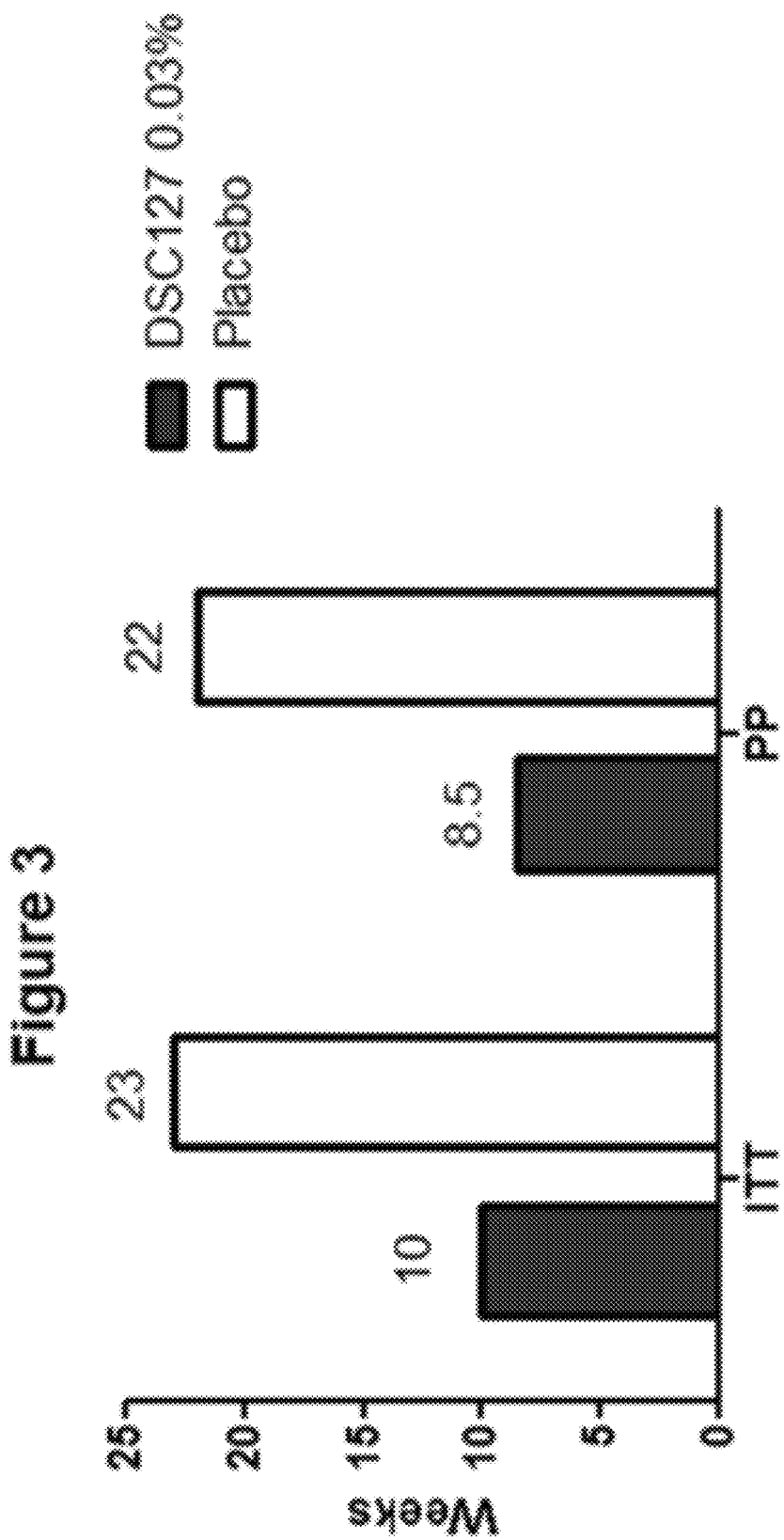

METHODS FOR TREATING DIABETIC FOOT ULCERS

CROSS REFERENCE

This application is a divisional of U.S. application Ser. No. 13/364,061 filed Feb. 1, 2012, and claims priority to U.S. Provisional Patent Application Ser. No. 61/438,780 filed Feb. 2, 2011, incorporated by reference herein in its entirety.

BACKGROUND

Diabetes is common, disabling and deadly. In the U.S., diabetes has reached epidemic proportions. According to the American Diabetes Association, about 24 million people (8% of the total U.S. population) have diabetes, and nearly two million new cases are diagnosed in people aged 20 years or older each year. If current trends continue, 1 in 3 Americans will develop diabetes at some point in their lifetime, and those with diabetes will lose, on average, 10-15 years of life expectancy. Importantly, up to 25% of people with diabetes will develop a diabetic foot ulcer, resulting in 3 million diabetic foot ulcers annually in the U.S. alone. More than half of all foot ulcers will become infected, thus requiring hospitalization, and 1 in 5 will require an amputation that carries a high risk of mortality.

Without question, diabetes puts tremendous economic pressure on the U.S. healthcare system. Total costs (direct and indirect) of diabetes have reached $174 billion annually, and people with diagnosed diabetes have medical expenditures that are over two times higher than medical expenditures for people without diabetes. Hospitalization costs alone are $16,000 to $20,000 for a patient with a diabetic foot ulcer, and direct and indirect costs of an amputation range from $20,000 to $60,000 per patient. A recent study by researchers at the University of Chicago suggested that treatment costs for diabetes in the United States would reach $336 billion by the year 2034. Advanced, cost-effective treatment modalities for diabetes and its co-morbidities, including diabetic foot ulcers, are in great need, yet in short supply, globally. According to the American Diabetes Association, by the year 2025 the prevalence of diabetes is expected to rise by 72% to 324 million people worldwide.

SUMMARY OF THE INVENTION

In a first aspect, the present invention provides methods for treating diabetic foot ulcers, comprising administering to a human patient suffering from a diabetic foot ulcer an amount of a peptide of at least 5 contiguous amino acids of Nle3 A(1-7), or salt thereof, effective to treat the diabetic foot ulcer. In one embodiment, the peptide comprises Asp-Arg-Nle-Tyr-Ile-His-Pro (SEQ ID NO:1), or salt thereof. In another embodiment, the peptide consists of Asp-Arg-Nle-Tyr-Ile-His-Pro (SEQ ID NO:1), or salt thereof. In various embodiments, the diabetic foot ulcer is one caused, at least in part, by neuropathy and resulting pressure; the diabetic foot ulcer comprises one or more calluses; and the diabetic foot ulcer is a chronic ulcer. In a further embodiment, the chronic foot ulcer has not responded to any other treatment.

In another embodiment, the peptide is administered topically. In a further embodiment, the peptide is administered as a topical formulation forming a continuous film covering the entire area of the diabetic ulcer. In a still further embodiment, the peptide is administered in a hydrogel formulation. In another embodiment, the peptide is administered at a concentration of about 0.03% to about 1% on a weight (mg)/volume (ml) basis, or on a weight/weight (mg) basis. In a further embodiment, the peptide is administered in a gel formulation that about 0.5% to about 4% hydroxyethyl cellulose (HEC) on a weight (mg)/volume (ml) basis, or on a weight/weight (mg) basis.

All embodiments of the first aspect of the invention can be combined unless the context dictates otherwise.

In a second aspect, the present invention provides pharmaceutical formulations, comprising:

(a) about 0.5% to about 4% HEC on a weight (mg)/volume (ml) basis, or on a weight/weight (mg) basis; and (b) a peptide of at least 5 contiguous amino acids of Nle3 A(1-7), or salt thereof;

wherein the peptide is present at a concentration of about 0.03% to about 1% on a weight (mg)/volume (ml) basis, or on a weight/weight (mg) basis.

In one embodiment, the peptide comprises Asp-Arg-Nle-Tyr-Ile-His-Pro (SEQ ID NO:1), or salt thereof. In another embodiment, the peptide consists of Asp-Arg-Nle-Tyr-Ile-His-Pro (SEQ ID NO:1), or salt thereof. In a further embodiment, the pharmaceutical formulation comprises about 1% to about 3% HEC on a weight (mg)/volume (ml) basis, or on a weight/weight (mg) basis. In a still further embodiment, the pharmaceutical formulation comprises about 2% HEC on a weight (mg)/volume (ml) basis, or on a weight/weight (mg) basis. In another embodiment, the formulation comprises a hydrogel formulation. All embodiments of the second aspect of the invention can be combined unless the context dictates otherwise.

BRIEF DESCRIPTION OF THE FIGURES

FIG. 2 is a graph showing the percentage of fully healed ulcers (100% wound closure) in the patient population taking NorLeu$^3$-A(1-7) (also referred to as "DSC127").

FIG. 3 is a graph showing the median time to fully healed ulcers (100% wound closure) in the patient population taking NorLeu$^3$-A(1-7) (also referred to as "DSC127").

DETAILED DESCRIPTION OF THE INVENTION

Figure 1:
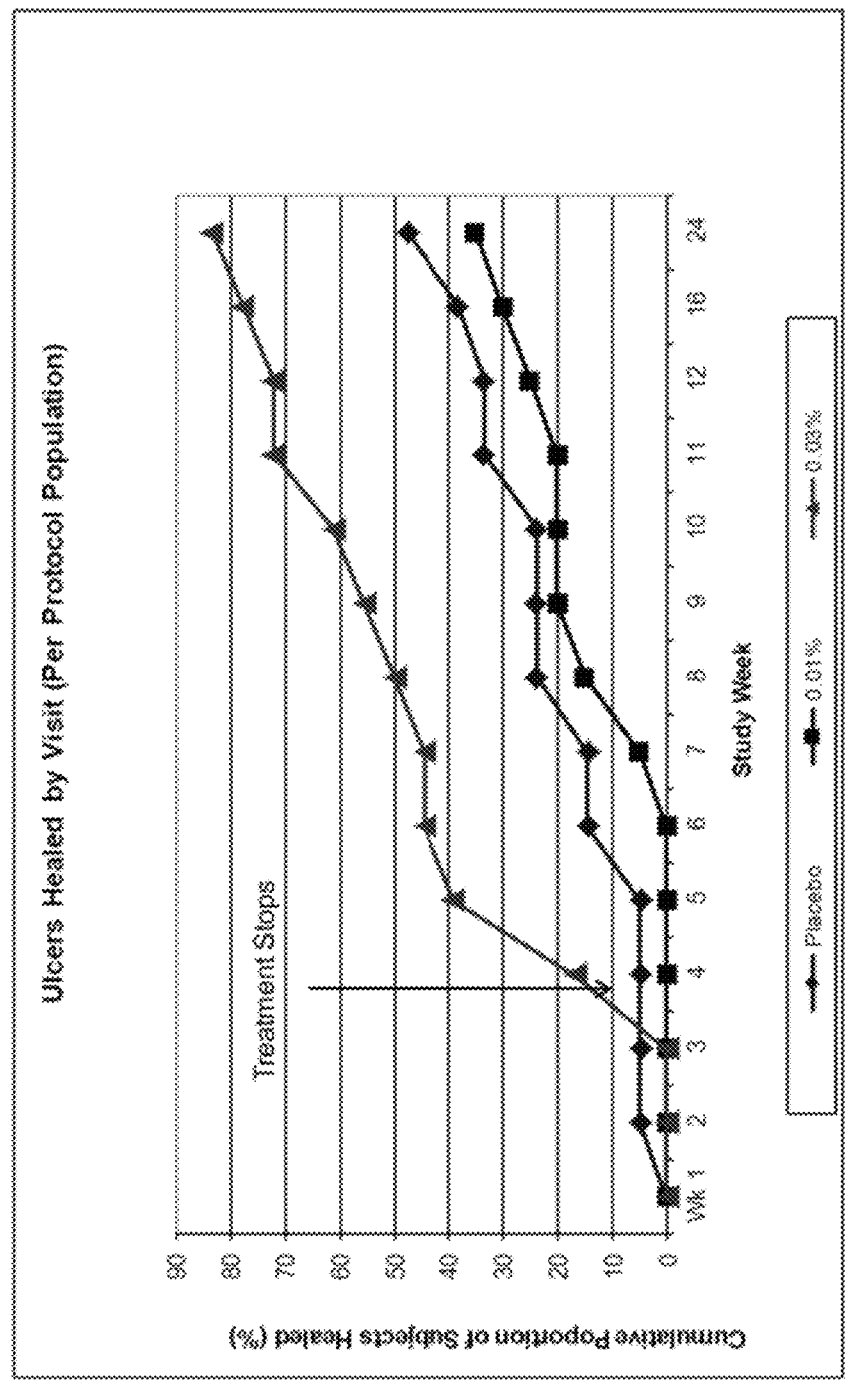
FIG. 1 is a graph showing the ulcers healed by visit in the Per Protocol (PP) patient population taking NorLeu$^3$-A(1-7).

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides methods for treating diabetic foot ulcers, comprising administering to a human patient suffering from a diabetic foot ulcer an amount of a peptide of at least 5 contiguous amino acids of Nle3 A(1-7), or salt thereof, effective to treat the diabetic foot ulcer.

As demonstrated in the examples that follow, the inventors have demonstrated that the methods of the invention can be used to treat diabetic foot ulcers, and provide substantial improvement over standard therapies.

Nle3A(1-7) (or NorLeu$^3$-A(1-7); also referred to as "DSC127") is a peptide consisting of the amino acid sequence Asp-Arg-Nle-Tyr-Ile-His-Pro (SEQ ID NO:1). In various embodiments, the peptide administered to the human patient may comprise or consist of Asp-Arg-Nle-Tyr-Ile (SEQ ID NO:2), Asp-Arg-Nle-Tyr-Ile-His (SEQ ID NO:3), or most preferably Asp-Arg-Nle-Tyr-Ile-His-Pro (SEQ ID NO:1), or salts thereof. Nle3A(1-7) or salts thereof may be chemically synthesized or recombinantly expressed, each of which can be accomplished using standard methods in the art.

In one embodiment, the peptide, or salt thereof, is administered at a concentration of about 0.03% to about 1% on a weight (mg)/volume (ml) basis, or on a weight/weight (mg) basis. In various further embodiments, the peptide, or salt thereof, is administered at a concentration of about 0.03% to about 0.75%; about 0.03% to about 0.5%; about 0.03% to about 0.25%; about 0.03% to about 0.1%; about 0.03% to about 0.075%; about 0.03% to about 0.05%; and about 0.03%; all on a weight (mg)/volume (ml) basis, or on a weight/weight (mg) basis.

The human patient may be suffering from Type I diabetes or Type II diabetes, and has a foot ulcer, defined as an open wound anywhere on the foot (heel, mid-foot, and forefoot).

As used herein, "treating" a diabetic foot ulcer includes
(a) limiting the progression in size, area, and/or depth of the foot ulcer;
(b) reducing size, area, and/or depth of the foot ulcer;
(c) increasing rate of healing and/or reducing time to healing;
(d) healing of the foot ulcer (100% epithelialization with no drainage); and
(e) decreased incidence of amputation or slowing in time to amputation.

The foot ulcer may be caused by any underlying pathology, including but not limited to neuropathy, trauma, deformity, high plantar pressures, callus formation, edema, and peripheral arterial disease. In preferred embodiments, the human diabetic foot ulcer is one caused, at least in part, by neuropathy and resulting pressure (weight bearing on the extremity due to lack of feeling in the foot). As is known to those of skill in the art, human diabetic foot ulcers tend to be due to neuropathy and pressure, which differs significantly from, for example, murine acute wounds. In a further preferred embodiment, the diabetic foot ulcer comprises one or more calluses.

In a further embodiment, the diabetic foot ulcer is a chronic ulcer. As used herein, a "chronic" foot ulcer is one that has been present for at least 7 days with no reduction in size; preferably at least 14 days; even more preferably, present at least 21 or 28 days with no reduction in size. In a further preferred embodiment that can be combined with any of these embodiments, the chronic foot ulcer has not responded (ie: no reduction in size, area, and/or depth of the foot ulcer; no healing of the foot ulcer) to any other treatment.

The peptide or salt thereof may be administered by any suitable route, preferably via topical administration. In one embodiment, the methods of the invention can comprise administering a topical formulation as often as deemed appropriate, ie: once per day, twice per day, etc. The methods may further comprise administration of the peptide, or salt thereof for as longed as deemed desirable by an attending physician, for example, until healing of the ulcer. For administration, it is preferred that the topical formulation form a continuous film covering the entire area of the ulcer, including the margins. In a preferred embodiment, the topical formulation is applied with a thickness of approximately 0.25 to 2 mm; preferably 0.5 to 1.5 mm; preferably about 1 mm in thickness.

In one embodiment, the topical administration comprises administration in a formulation selected from the group consisting of hydrogels, creams, ointments, pastes, and lotions. The formulations may be applied in any suitable manner, which may include any wound dressings to seal in the formulation deemed appropriate by the human patient or caregiver. Exemplary such dressings, include, but are not limited to, semipermeable films, foams, hydrocolloids, and calcium alginate swabs.

The methods may further comprise debridement in and around the wound in combination with administration of the peptide and formulations thereof. Debridement of all necrotic, callus, and fibrous tissue is typically carried for treatment of diabetic foot ulcers. Unhealthy tissue is sharply debrided back to bleeding tissue to allow full visualization of the extent of the ulcer and to detect underlying abscesses or sinuses. Any suitable debridement technique can be used, as determined by an attending physician. The wound can then be thoroughly flushed with sterile saline or a non-cytotoxic cleanser following debridement.

In another embodiment, the topical formulation comprises about 0.5% to about 4% hydroxyethyl cellulose (HEC) on a weight (mg)/volume (ml) basis, or on a weight/weight (mg) basis. In various further embodiments, the topical formulation may comprise about 1% to about 3% HEC, or about 2% HEC, on a weight (mg)/volume (ml) basis, or on a weight/ weight (mg) basis. These formulations comprising low percentage HEC (ie: 2%) matrices provided a 10-fold increase in peptide release over a 24 hour period from formulations such as those comprising 10% carboxymethylcellulose (CMC), a result that would be unexpected to those of skill in the art. Furthermore, the data show that the HEC matrices are more biocompatible than HPMC and CMC formulations tested.

The peptides, or salt thereof may be administered together with one or more (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The peptides may be administered with a lyoprotectant, e.g. sucrose, sorbitol or trehalose. In certain embodiments, the peptides may be administered with a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the peptides may be administered with a bulking agent, like glycine. In yet other embodiments, the peptides may be administered with a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The peptides may be administered with a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the peptides may be administered with a stabilizer, e.g., a molecule which, when combined with the peptide substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride, paraben, and combinations of methyl paraben and propyl paraben.

In all aspects and embodiments of the invention, suitable acids which are capable of forming salts with the peptides include, but are not limited to, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming salts with the peptides include, but are not limited to, inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The peptides or salts thereof can further be derivatized to provide enhanced half-life, for example, by linking to polyethylene glycol. The peptides or salts thereof may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties.

The polypeptides may be the sole active agent in the pharmaceutical composition, or the composition may further comprise one or more other active agents suitable treating diabetic foot ulcers, such as antibiotics. The methods may be used in conjunction with other foot ulcer therapies, including but not limited to negative pressure wound therapy, total contact casts, removable cast walkers, half-shoes, becaplermin, infection control, and hyperbaric oxygen therapy.

The methods may include any other embodiments as disclosed in the example that follows. Such embodiments may be used in any combination in the methods of the invention, unless the context clearly dictates otherwise.

In a second aspect, the present invention provides pharmaceutical formulations, comprising:

(a) about 0.5% to about 4% HEC on a weight (mg)/volume (ml) basis, or on a weight/weight (mg) basis; and (b) a peptide of at least 5 contiguous amino acids of Nle3 A(1-7), or salt thereof;

wherein the peptide is present at a concentration of about 0.03% to about 1% on a weight (mg)/volume (ml) basis, or on a weight/weight (mg) basis.

The pharmaceutical formulations are demonstrated herein to be particularly effective for treating diabetic foot ulcers, such as chronic diabetic foot ulcers that are not effectively treated using standard therapies.

In one embodiment, the peptide comprises Asp-Arg-Nle-Tyr-Ile-His-Pro (SEQ ID NO:1), or salt thereof. In another embodiment, the peptide consists of Asp-Arg-Nle-Tyr-Ile-His-Pro (SEQ ID NO:1), or salt thereof.

In one embodiment, the peptide, or salt thereof, is present in the formulation at a concentration of about 0.03% to about 1% on a weight (mg)/volume (ml) basis, or on a weight/weight (mg) basis. In various further embodiments, the peptide, or salt thereof, is present in the formulation at a concentration of about 0.03% to about 0.75%; about 0.03% to about 0.5%; about 0.03% to about 0.25%; about 0.03% to about 0.1%; about 0.03% to about 0.075%; about 0.03% to about 0.05%; and about 0.03%; all on a weight (mg)/volume (ml) basis, or on a weight/weight (mg) basis.

In a further embodiment, the pharmaceutical formulation comprises about 1% to about 3% HEC on a weight (mg)/volume (ml) basis, or on a weight/weight (mg) basis. These formulations comprising low percentage HEC (ie: 2%) matrices provided a 10-fold increase in peptide release over a 24 hour period from formulations such as those comprising 10% carboxymethylcellulose (CMC), a result that would be unexpected to those of skill in the art. Furthermore, the data show that the HEC matrices are more biocompatible than HPMC and CMC formulations tested. In a still further embodiment, the pharmaceutical formulation comprises about 2% HEC on a weight (mg)/volume (ml) basis, or on a weight/weight (mg) basis. In another embodiment, the formulation comprises a hydrogel formulation.

In one embodiment, the formulation is topical gel-based formulation selected from the group consisting of hydrogels, creams, ointments, pastes, and lotions. The formulation is administered so as to form a continuous film covering the entire area of the ulcer, including the margins, without running off. In a preferred embodiment, the topical formulation is applied with a thickness of approximately 0.25 to 2 mm; preferably 0.5 to 1.5 mm; preferably about 1 mm in thickness. In another non-limiting embodiment the formulation is applied at approximately 0.075 mL per cm$^2$ surface area.

In all aspects and embodiments of the invention, suitable acids which are capable of forming salts with the peptides include, but are not limited to, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming salts with the peptides include, but are not limited to, inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The pharmaceutical formulations may further comprise (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical formulations is a Tris buffer, a histidine buffer, a phosphate buffer, a citrate buffer or an acetate buffer. The pharmaceutical formulations may also include a lyoprotectant, e.g. sucrose, sorbitol or trehalose. In certain embodiments, the pharmaceutical formulations includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical formulations includes a bulking agent, like glycine. In yet other embodiments, the pharmaceutical formulations includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical formulations may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical formulations additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The peptides or salts thereof can further be derivatized to provide enhanced half-life, for example, by linking to polyethylene glycol. The peptides or salts thereof may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties.

The peptide may be the sole active agent in the pharmaceutical composition, or the composition may further comprise one or more other active agents suitable for treating diabetic ulcers.

The formulations may include any other embodiments as disclosed in the example that follows. Such embodiments may be used in any combination in the formulations of the invention, unless the context clearly dictates otherwise.

Example

Randomized, Parallel-Group, Double-Blind, Placebo-Controlled Phase 2 Clinical Trial to Evaluate the Safety and Effectiveness of NorLeu$^3$-A(1-7) in Treating Subjects with Diabetic Ulcers The study was designed as a randomized, parallel-group, double-blind, placebo-controlled, multi-center trial. After 14-days of best-of-care to evaluate ulcer healing and ensure the wounds were chronic, four-weeks of active treatment were then followed by eight weeks of observation and assessment. The study compared the effects of two concentrations of NorLeu$^3$-A(1-7) and placebo, measuring both clinical efficacy and safety. Sustained tissue integrity was evaluated for all subjects during a follow-up period lasting 12 weeks after complete wound closure.

Subjects were randomized in a 1:1:1 ratio to one of the three treatment groups:
Group 1: Placebo Vehicle Control without NorLeu$^3$-A(1-7) (also referred to as "DSC127") (2% Hydroxyethyl Cellulose (HEC) with 0.1% methyl paraben, 0.02% propyl paraben)
Group 2: 0.03% NorLeu$^3$-A(1-7) in Vehicle
Group 3: 0.01% NorLeu$^3$-A(1-7) in Vehicle The four-week treatment period required daily application of the treatment to the wound site. The first application each week was at the clinic and for the remainder of the week the patient self-administered the treatment.

If wound healing occurred during the treatment or assessment periods a final assessment visit was conducted and the integrity was assessed 4 and 12 weeks later (usually weeks 16 and 24 of the study).

Inclusion Criteria

The following patients were considered eligible for participation in the study:
1) Male or female ambulatory subjects who were at least 18 years of age at screening
2) At start of Screening Period and upon enrollment into the study, had at least one chronic non-healing Wagner Grade 1 or Grade 2 (ulcers of partial or full thickness and not involving bone, tendon or capsule (probing to tendon or capsule), and that have no sign of infection or myelitis) plantar neuropathic diabetic ulcer between 1.0-6.0 cm$^2$ on the midfoot or forefoot, including the toes but excluding the heel. Non-healing is defined as present for a minimum of one month but not longer than ten months with less than 30% reduction in size in response to treatment (non-study treatment, but including off-loading) during the Screening Period. If more than one ulcer is present that meets the inclusion criteria, the larger was studied and treated according to the protocol. Non-study ulcers were treated according to institutional best practice, using per protocol offloading.
3) Have an Ankle Brachial Index (ABI) greater than 0.7 for neuroischemic or greater than 0.8 for neuropathic DFU.
4) Have a Tissue Oxygen Pressure (TcPO$_2$) greater than 40 mm Hg or great toe systolic pressure greater than 50 mmHg to ensure healing potential.
5) Have Type I or Type II diabetes under metabolic control as confirmed by a glycosylated hemoglobin (HbAlc) of less than or equal to 12%, and a serum creatinine level of no greater than 3 mg/dL obtained within 3 months of study enrollment.
6) Assess the baseline level of neuropathy of the foot using Semmes-Weinstein filaments. Patients were considered to have site specific neuropathy sufficient for loss of protective sensation (LOPS) if they were unable to feel a #5.07 monofilament applied to at least 5 of the following 7 sites (28) on the study foot:
plantar to toes and metatarsals 1, 3 and 5 (3 sites)
plantar to midfoot medial and lateral (2 sites)
plantar heel (1 site)
dorsal distal first interspace (1 site)
7) Female subjects of child-bearing potential must have negative pregnancy test at the time of initiation of study therapy.
8) Female subjects of child-bearing potential must have been willing to use a medically acceptable method of birth control, such as Essure®, hormonal contraception (oral pills, implantable device or skin patch), intrauterine device, tubal ligation or double barrier, during the treatment and assessment period of study participation.
9) Ability and willingness to understand and comply with study procedures and to give written informed consent prior to enrollment in the study or initiation of study procedures.

Exclusion Criteria

If a subject met any of the following criteria, he or she was excluded from the study:
1) Has a known hypersensitivity to any of the study medication components.
2) Exposure to any investigational agent within 30 days of entry into study.
3) Females who are pregnant or nursing.
4) Females unwilling to use a medically acceptable method of birth control, such as Essure®, hormonal contraception (oral pills, implantable device or skin patch), intrauterine device, tubal ligation or double barrier, during the treatment and assessment period of study participation.

5) Active malignant disease of any kind A subject, who has had a malignant disease in the past, was treated and is currently disease-free, may be considered for study entry.
6) Chronic renal insufficiency (serum creatinine during screening is greater than 3.0 g/dL obtained within 3 months of study enrollment).
7) Chronic liver dysfunction evidenced by transaminase levels greater than twice normal.
8) Receiving hemodialysis or chronic ambulatory peritoneal dialysis (CAPD) therapy.
9) Resting blood pressure (at the time of the initial visit of the Screening Period) which exceeds 160 systolic and/or 90 diastolic mmHg on 3 consecutive readings at least 15 minutes apart.
10) Prior radiation therapy of the foot with the ulcer under study.
11) Current use of corticosteroids (within past 8 weeks), immunosuppressants (within past 8 weeks).
12) Known to be HIV positive.
13) Subjects whose ulcer was primarily ischemic in etiology as diagnosed by an ABI of <0.7 or great toe systolic pressure<40 mmHg or TcPO2<40 mmHg in the supine position and <40 mmHg while sitting, measured on the forefoot with electrode set at 44 C.
14) Sickle-cell anemia, Raynaud's or other peripheral vascular disease.
15) Current history of drug abuse.
16) Subjects receiving a biologic agent to include growth factors and skin equivalents (Regranex™, Apligraft™, or Dermagraft™) in the past 30 days.
17) Subjects with uncontrolled diabetes defined as a glycosylated hemoglobin (HbAlc)>12%, or a serum creatinine level of greater than 3 g/dL obtained within 3 months of study enrollment determined on two separate occasions at least 3 weeks apart.
18) Subject with an ulcer which is determined to be clinically infected and requires topical antimicrobials or agents known to affect wound healing or has been taking systemic antibiotics for more than 7 days for any reason.
19) Subject with a Wagner Grade 3 or higher DFU, deep abscess or infection of the joint or tendon, or gangrene or osteomyeltitis.
20) An EKG with a marked baseline prolongation of QT/QTc interval (e.g., repeated demonstration of QTc interval>450 milliseconds (ms))

A total of 80 subjects were enrolled in the study; 27 were randomized to the 0.03% dose of NorLeu$^3$-A(1-7), 25 were randomized to placebo and 28 were randomized to the 0.01% dose. All subjects also received best standard of care, which included debridement, wound cleansing, application of an occlusive dressing and standardized proper off-loading.

Results

Recent results from a Phase 2 clinical trial with NorLeu$^3$-A(1-7) in patients with diabetic foot ulcers showed that the proportion of study ulcers healed by 12 weeks as defined by 100% epithelialized with no drainage, as well as all secondary endpoints. The double-blind, placebo-controlled, multi-center clinical trial randomized 80 subjects to receive one of two doses of NorLeu$^3$-A(1-7) (0.03% and 0.01%) or vehicle placebo (2% hydroxyethyl cellulose in phosphate buffer with 0.1% methyl paraben and 0.02% propyl paraben) control, in addition to best standard of care (which included debridement). The drug was well-tolerated and there were no significant adverse events associated with NorLeu$^3$-A(1-7) treatment.

In the Intent-to-Treat (ITT) population (all subjects receiving any study medication and from whom any post-baseline data are available): Results show that 54% of the diabetic wounds treated with 0.03% (high dose) of NorLeu$^3$-A(1-7) achieved 100% closure in 12 weeks or less, compared with 33% of patients receiving placebo control, and 30% of patients receiving the 0.01% dose (low dose) of NorLeu$^3$-A(1-7). Based on odds ratio analysis, patients treated with NorLeu$^3$-A(1-7) 0.03% were 2.3 times more likely to have their wounds heal completely as compared to patients treated with placebo/standard of care.

In the Per Protocol (PP) population (all patients that did not have a major protocol violation affecting efficacy): Results show that 65% of the diabetic wounds treated with 0.03% dose of NorLeu$^3$-A(1-7) achieved 100% closure in 12 weeks or less, compared with 38% of patients receiving placebo control, and 28% of patients receiving the 0.01% dose of NorLeu$^3$-A(1-7). See FIGS. 1-3. Based on odds ratio analysis, patients treated with NorLeu$^3$-A(1-7) 0.03% were 3.0 times more likely to have their wounds heal completely as compared to patients treated with placebo/standard of care.

The high dose of NorLeu$^3$-A(1-7) well exceeded the trial's primary endpoint measurement target of an improvement of 15 percentage points in complete healing of wounds within the 12-week duration of the study for both the ITT (21% increase) and PP (27% increase) populations compared with placebo.

The trial was not powered for statistical significance, however there was a statistically significant (p=0.049) 50% improvement in the rate of healing in the PP high-dose population through 12 weeks of treatment compared with the control arm, as measured by depth of ulcer using covariate analysis.

The wound healing rates for patients on NorLeu$^3$-A(1-7) were remarkable with the ITT analysis showing a 21% increase and the PP analysis showing a 27% increase over the placebo arm.

REFERENCES

1. American Diabetes Association, Consensus development conference on diabetic foot wound care. *Diabetes Care* 1999; 22:1354-1360.
2. Pecoraro R E, Reiber G E, Burgess E M, Pathways to diabetic limb amputation: basis for prevention. *Diabetes Care* 1990; 13:513-521.
3. Rodgers K E, Roda N, Felix J C, Espinoza T, Maldonado S, diZerega G S. Histological evaluation of the effects of angiotensin peptides on wound repair in diabetic mice. *Experimental Dermatology* 2003; 12(6):784-790.
4. Rodgers K, Xiong S, Felix J, Roda N, Espinoza T, Maldonado S, diZerega G S. Development of angiotensin (1-7) as an agent to accelerate dermal repair. *Wound Repair Regen* 2001; 9:238-250.
5. Rodgers K E, Espinoza T, Felix J, Roda N, Maldonado S, diZerega G S. Acceleration of healing, reduction of fibrotic scar, and normalization of tissue architecture by an angiotensin analogue, Norleu$^3$-A (1-7). *Plast Reconstr Surg* 2003; 111:1195-1206.
6. Wagner, F J. A classification and treatment program for diabetic, neuropathic, and dysvascular foot problems. *Am Acad of Orthopaedic Surgeons. Instructional Course Lecture* 1979; 28:143-165.
7. Foster A V, Eaton C, McConville D O, Edmonds M E. Application of OpSite film: a new and effective treatment of painful diabetic neuropathy. *Diabetes Med* 1994; 11(8): 768-772.

8. Sheehan P, Jones P, Caselli A, Giurini J M, Veves A. Percent change in wound area of diabetic foot ulcers over a 4-week period is a robust predictor of complete healing in a 12-week prospective trial. *Diabetes Care* 2003; 26:1879-1882.
9. Rodgers, K E, Abiko M, Girgis W, St. Amand K M, Campeau J D, diZerega G S. Acceleration of dermal tissue repair by Angiotensin II. *Wound Repair Regen* 1997; 5:175-183.
10. Rodgers, K E, DeCherney A H, St. Amand K M, Dougherty W R, Felix J C, Girgis W, diZerega G S. Histologic alterations in dermal repair after thermal injury: effects of topical angiotensin II. *Burn Care and Rehabilitation* 1997; 18:381-388.
11. Okuyama N, Roda N, Guerrero A, Dougherty W, Nguyen T, diZerega G S, Rodgers K E. Effect of angiotensin II on the viability, vascularity of random flaps in a rat model. Annals *Plastic Surgery Res* 1999; 68:913-918.
12. Rodgers K E, Ellefson D D, Espinoza T, Roda N, Maldonado S, diZerega G S. Effect of NorLeu$^3$-A (1-7) on scar formation over time after full thickness incision injury in the rat. *Wound Repair Regen* 2005; 13:309-317.
13. Santos R A, Brosnihan K B, Chappell M C, Pesquero J, Chemicky C L, Greene L J, and Ferrario C M. Converting enzyme activity and angiotensin metabolism in the dog brainstem. *Hypertension* 1988; 11(suppl I):I-53-I-57.
14. Santos R A S, Brosnihan K B, Jacobsen D W, DiCorleto P, and Ferrario C M. Production of Ang-(1-7) by human vascular endothelium. *Hypertension* 1992; 19(suppl II):II-56-II-61.
15. Santos et al. Characterization of a new angiotensin antagonist selective for angiotensin-(1-7): evidence that the actions of angiotensin-(1-7) are mediated by specific angiotensin receptors. *Brain Res Bull* 1994; 35:293-298.
16. Yamamoto K, Chappell M C, Brosnihan K B, Ferrario C M. In vivo metabolism of angiotensin I by neutral endopeptidase (EC 3.4.24.11) in spontaneously hypertensive rats. *Hypertension* 1992; 19:692-696.
17. Chappell M C, Tallant E A, Brosnihan K B, Ferrario C M. Processing of angiotensin peptides by NG108-15 neuroblastoma X glioma hybrid cell line. *Peptides* 1990; 22:375-380.
18. Chappell M C, Jacobsen D W, Tallant E A. Characterization of angiotensin II receptor subtypes in pancreatic acinar AR42J cells. *Peptides* 1995; 16:741-747.
19. Chappell M C, Tallant E A, Brosnihan K B, Ferrario C M. Conversion of angiotensin I to angiotensin-(1-7) by thimet oligopeptidase (E.C.3.4.24.15) in vascular smooth muscle cells. *J Vasc Biol Med* 1995; 5:129-137.
20. Daemen M J A P, Lombardi D M, Bosman F T, Schwartz S M. Angiotensin II induces smooth muscle cell proliferation in the normal and injured rat arterial wall. *Circ Res* 1991; 68:450-56.
21. Dzau V E, Pratt R, Gibbons G, Schunkert H, Lorell B, Ingelfinger J. Molecular mechanism of angiotensin in the regulation of vascular and cardiac growth. *J Mol Cell Cardiol* 1989; 21 [Suppl III]:57.
22. Naftilan A J, Pratt R E, Dzau V J. Induction of platelet-derived growth factor A-chain and c-myc gene expression by Angiotensin II in culture rat vascular smooth muscle cells. *J Clin Invest* 1989; 83:1419-24.
23. Stouffer G A, Owens G K. Angiotensin II induced mitogenesis of spontaneously hypertensive rat derived cultured smooth muscle cells is dependent on autocrine production of transforming growth factor-$\beta$. *Circ Res* 1992; 70:820-28.
24. Koibuchi Y, Lee W S, Gibbons G H, Pratt R E. Role of transforming growth factor $\beta$-1 in the cellular growth response to Angiotensin II. *Hypertension* 1993; 21:1046-50.
25. Kawahara Y, Sunako M, Tsuda T, Fukazaki H, Fukomoto Y, Takai Y. Angiotensin II induces expression of the c-fos gene through protein kinase C activation and calcium ion mobilization in cultured vascular smooth muscle cells. *BBRC* 1988; 150:52-9.
26. Mangiarua E I, Palmer V L, Lloyd L L, McCumbee W D. Platelet-derived growth factor mediates angiotensin II-induced DNA synthesis in vascular smooth muscle cells. *Arch Physiol Biochem* 1997; 105(2):151-7.
27. Su E J, Lombardi D M, Wiener J, Daemen M J, Reidy M A, and Schwartz M A. Mitogenic effect of angiotensin II on the rat carotid arteries and type II or III mesenteric microvessels but not type I mesenteric microvessels is mediated by endogenous basic fibroblast growth factor. *Circ Res* 1998; 82:321.
28. Rodgers L C. Driver V R, Armstrong D G. Assessment of the diabetic foot. In Krasner D L, Rodeheaver G T, Sibbald R G eds. Chronic Wound Care: A Clinical Source Book for Healthcare Professionals. 4$^{th}$ ed. Malvern Pa.: HMP Communications, 2007: 549-556.
29. Bolton L, McNees P, van Rijswijk L et al. Wound healing outcomes using standardized care. *JWOCN* 2004; 31:65-71.

We claim:

1. A pharmaceutical formulation, comprising:
   (a) about 0.5% to about 4% HEC on a weight (mg)/volume (ml) basis, or on a weight/weight (mg) basis; and
   (b) a peptide of at least 5 contiguous amino acids of Nle3 A(1-7);
   wherein the peptide is present at a concentration of about 0.03% to about 1% on a weight (mg)/volume (ml) basis, or on a weight/weight (mg) basis.

2. The pharmaceutical formulation of claim 1, wherein the peptide comprises Asp-Arg-Nle-Tyr-Ile-His-Pro (SEQ ID NO:1).

3. The pharmaceutical formulation of claim 1, wherein the peptide consists of Asp-Arg-Nle-Tyr-Ile-His-Pro (SEQ ID NO:1).

4. The pharmaceutical formulation of claim 1, comprising about 1% to about 3% HEC on a weight (mg)/volume (ml) basis, or on a weight/weight (mg) basis.

5. The pharmaceutical formulation of claim 1, comprising about 2% HEC on a weight (mg)/volume (ml) basis, or on a weight/weight (mg) basis.

6. The pharmaceutical formulation of claim 1, wherein the formulation comprises a hydrogel formulation.

7. The pharmaceutical formulation of claim 2, comprising about 1% to about 3% HEC on a weight (mg)/volume (ml) basis, or on a weight/weight (mg) basis.

8. The pharmaceutical formulation of claim 2, comprising about 2% HEC on a weight (mg)/volume (ml) basis, or on a weight/weight (mg) basis.

9. The pharmaceutical formulation of claim 2, wherein the formulation comprises a hydrogel formulation.

10. The pharmaceutical formulation of claim 3, comprising about 1% to about 3% HEC on a weight (mg)/volume (ml) basis, or on a weight/weight (mg) basis.

11. The pharmaceutical formulation of claim 3, comprising about 2% HEC on a weight (mg)/volume (ml) basis, or on a weight/weight (mg) basis.

12. The pharmaceutical formulation of claim 3, wherein the formulation comprises a hydrogel formulation.

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle

<400> SEQUENCE: 1

Asp Arg Xaa Tyr Ile His Pro
1               5
```

```
<210> SEQ ID NO 2
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle

<400> SEQUENCE: 2

Asp Arg Xaa Tyr Ile
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle

<400> SEQUENCE: 3

Asp Arg Xaa Tyr Ile His
1               5
```